United States Patent [19]

Kaschig et al.

[11] Patent Number: 4,590,129
[45] Date of Patent: May 20, 1986

[54] FLUOROALIPHATIC-THIO,-SULFINYL, OR SULFONYL SUBSTITUTED BICYCLOALIPHATIC AMIC ACID AMINE SALTS, AND COMPOSITIONS AND USE THEREOF

[75] Inventors: Jürgen Kaschig, Freiburg, Fed. Rep. of Germany; Eduard K. Kleiner, Pound Ridge, N.Y.; Karl F. Mueller, New York, N.Y.; Thomas W. Cooke, Mahopac, N.Y.

[73] Assignee: Ciba-Geigy Corporation, Ardsley, N.Y.

[21] Appl. No.: 692,256

[22] Filed: Jan. 17, 1985

Related U.S. Application Data

[62] Division of Ser. No. 503,435, Jun. 13, 1983, Pat. No. 4,515,640.

[51] Int. Cl.$^4$ ............ D21D 3/00; B32B 9/02; B32B 27/00
[52] U.S. Cl. ............ 428/425.1; 162/164.6; 162/166; 162/175; 428/473; 428/474.4; 428/537.5
[58] Field of Search ............ 162/164.6, 166, 175; 428/537.5, 425.1, 473, 474.4

[56] References Cited

U.S. PATENT DOCUMENTS 4,515,640 5/1985 Kaschig et al. ............ 106/208

Primary Examiner—Theodore Morris
Attorney, Agent, or Firm—Michael W. Glynn; Irving M. Fishman

[57] ABSTRACT

Fluoroaliphatic-thio,-sulfinyl and -sulfonyl substituted bicycloaliphatic amic acid amine salts of the formula

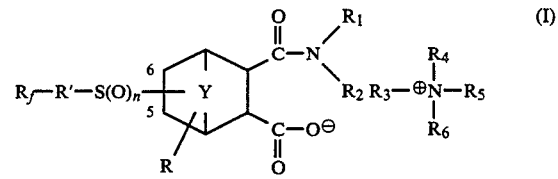

where $R_f$ is perfluoroalkyl, R' is alkylene optionally interrupted by —O—, —S— or

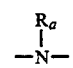

where $R_a$ is hydrogen or alkyl, Y is lower alkylene or —O—, n is 0–2, $R_1$ and $R_2$ are independently hydrogen, lower alkyl, hydroxy lower alkyl or together with the nitrogen to which they are attached, represent morpholino, $R_3$, $R_4$ and $R_5$ are independently hydrogen, lower alkyl, or hydroxy lower alkyl, $R_6$ is lower alkyl, carboxy lower alkyl, sulfo lower alkyl, hydroxy lower alkyl, benzyl or together with $R_5$ and the nitrogen to which they are attached represent morpholino, and R is hydrogen or methyl are provided. These salts applied in the form of aqueous solutions, dispersions or emulsions are useful in rendering cellulosic and natural and synthetic polyamide materials oil and water repellent.

8 Claims, No Drawings

FLUOROALIPHATIC-THIO,-SULFINYL, OR SULFONYL SUBSTITUTED BICYCLOALIPHATIC AMIC ACID AMINE SALTS, AND COMPOSITIONS AND USE THEREOF

This is a divisional of application Ser. No. 503,435 filed on June 13, 1983, now U.S. Pat. No. 4,515,640.

BACKGROUND OF THE INVENTION

The instant invention relates to fluoroaliphatic-thio,-sulfinyl, or -sulfonyl substituted bicycloaliphatic amic acid amine salts, and the manufacture and use of such salts in the form of aqueous solutions, emulsions or dispersions in treating cellulosic materials and natural or synthetic polyamide materials to render the same oil and water repellent.

Fluoroaliphatic-thio substituted bicycloaliphatic anhydrides, useful as starting materials in the manufacture of the instant amic acid amine salts, are, in part, disclosed in U.S. Pat. No. 4,082,798, the disclosure of which is incorporated by reference herein.

While the anhydrides, or corresponding diacids of this U.S. patent, when converted to simple metal salts show pronounced surfactant activity, they are unsuitable for the formation of stable aqueous solutions, emulsions or dispersions to render cellulosic or polyamide materials hydrophobic and oleophobic. Moreover, the imides, diamides and diesters exemplified in this reference possess, in general, very limited water solubility and are thus unsuitable for use as aqueous solutions, emulsions or dispersions in accordance with the instant invention.

It is therefore an object of the instant invention to provide the artisan with novel fluoroaliphatic containing bicycloaliphatic amic acid amine salts, and stable aqueous solutions, emulsions or dispersions containing the same as well as the use thereof in rendering cellulosic and polyamide materials oil and water repellent.

It is a further object of the present invention to provide the artisan with efficient fluorochemical containing aqueous solutions, dispersions and emulsions providing high fluorochemical pick-up properties on cellulosic and polyamide substrates.

It is a further object of the present invention to provide the artisan with fluorochemical treated cellulosic and polyamide containing materials possessing a high degree of oil and repellent properties, and a method of making the same.

It is yet a further object of the instant invention to provide the artisan with process for the preparation of these compounds.

These and other objects of the invention are apparent from the following disclosure.

DETAILED DISCLOSURE

One aspect of the instant invention relates to fluoroaliphatic substituted bicycloaliphatic amic acid amine salts of the formula

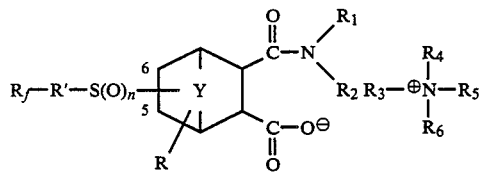

(I)

wherein $R_f$ is straight or branched chain perfluoroalkyl of 4 to 18 carbon atoms or perfluoroalkoxy-perfluoroalkyl of 4 to 18 carbon atoms;

$R'$ is straight or branched chain alkylene of 1 to 12 carbon atoms, alkylenethioalkylene of 2 to 12 carbon atoms, alkyleneoxyalkylene of 2 to 12 carbon atoms, or alkyleneiminoalkylene of 2 to 12 carbon atoms where the imino nitrogen atom contains as a third substituent, hydrogen or alkyl of 1 to 6 carbon atoms;

n is 0, 1 or 2;

Y is lower alkylene or —O—;

$R_1$ and $R_2$ are independently hydrogen, lower alkyl, hydroxy-lower alkyl, or together with the nitrogen to which they are attached, represent morpholino;

$R_3$, $R_4$ and $R_5$ independently represent hydrogen, lower alkyl, or hydroxy-lower alkyl, $R_6$ is lower alkyl, benzyl, lower alkyl substituted by hydroxy, carboxy or sulfo, or together with $R_5$ and the nitrogen to which they are attached represent morpholino;

R is hydrogen or methyl; and wherein the $R_f$—$R'$—$S(O)_n$— group is in the 5- or 6-position.

Preferably, $R_f$ is perfluoroalkyl of 6 to 14 carbon atoms, $R'$ is alkylene of 1 to 6 carbon atoms, n is 0 or 2, Y is methylene or ethylene, $R_1$ is hydrogen or hydroxy-lower alkyl, $R_2$ is hydroxy-lower alkyl, or $R_1$ and $R_2$ taken together are morpholino, $R_3$, $R_4$ and $R_5$ are independently hydrogen, lower alkyl or hydroxy-lower alkyl, $R_6$ is hydroxy-lower alkyl or together with $R_5$ and the nitrogen to which they are attached represent morpholino; and R is hydrogen or methyl.

More preferably, $R_f$ is 6 to 12 carbon atoms, $R'$ is alkylene of 2 to 4 carbon atoms, n is O, Y is methylene, $R_1$ is hydrogen or hydroxyethyl, $R_2$ is hydroxyethyl, or $R_1$ and $R_2$ taken together with the nitrogen to which they are attached represent morpholino, $R_3$ and $R_4$ are hydrogen, $R_5$ is hydrogen or hydroxyethyl, $R_6$ is hydroxyethyl or taken together with $R_5$ and the nitrogen to which they are attached represent morpholino, and R is hydrogen.

Most preferred are those compounds of the preceding paragraph wherein $R_1$, $R_2$, $R_5$ and $R_6$ are hydroxyethyl and $R_3$ and $R_4$ are hydrogen.

By "lower" in connection with an aliphatic group is meant those groups containing up to 6 carbon atoms, preferably up to 4 carbon atoms, most preferably 2 or 3 carbon atoms.

Examples of advantageous amine cations include
$H_3N^+CH_2CH_2OH$,
$H_2N^+(CH_2CH_2OH)_2$,
$HN^+(CH_2CH_2OH)_3$,
$N^+(CH_2CH_2OH)_4$,

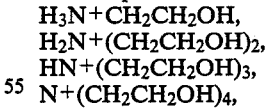

$H_3N^+CH_2CHOHCHOHCHOHCHOHCH_2OH$,
$CH_3N^+H_2CH_2CHOHCHOHCHOHCHOHCH_2OH$
$H_2N^+(CH_2CHOHCH_3)_2$,
$H_3N^+C(CH_2OH)_3$,
$H_3N^+C(CH_3)_2CH_2OH$,
$H_3N^+CH_2COOH$,
$HN^+(CH_2COOH)_3$, $H_3N^+-CH_2CH_2SO_3H$,
and the like.

In the compounds of formula I, the carbonyl groups in the 2- and 3-position of the bicycloaliphatic nucleus may be exo,exo; endo,endo; or exo,endo or mixtures thereof. Preferred are those compounds of formula I which are approximately 1:1 mixtures of the exo,exo and endo,endo isomers.

The compounds of formula I may be prepared by various methods.

In one embodiment, the compounds of formula I are prepared by reacting a mercaptan of the formula $$R_f-R'-S-H \quad \text{(II)}$$

wherein $R_f$ and $R'$ are as above defined, with a bicycloaliphatic amic acid or salt thereof of the formula

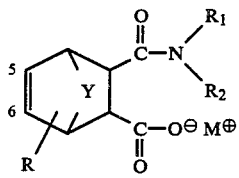
(III)

where Y, $R_1$, R and $R_2$ are as above defined, and $M^+$ is the cation of formula I, hydrogen, alkali metal, alkaline earth metal or ammonium cation.

The reaction ratio can vary widely, e.g. from 2:1 to 1:2 moles of II per mole of III, in the presence of an inert diluent such as water, or an aprotic solvent, e.g. dimethylformamide, dimethylsulfoxide, tetrahydrofuran, etc., a lower alkanoic acid, such as acetic acid, a lower alkanol, such as ethanol or isopropanol, or mixtures thereof, and a catalytic amount of a free radical initiator, at a temperature between about 0° C. to 100° C. Suitable free radical initiator include peroxides such as hydrogen peroxide, peracetic acid, benzoyl peroxide, azo catalysts such as 2-t-butylazo-2-cyanopropane.

To obtain those compounds of formula I wherein n is 1 or 2 from the compounds produced according to this reaction, the product is oxidized with one to two moles of oxidizing agent per mole of product at a temperature of about 0° C. to about 100° C. in the presence of a suitable inert diluent. Suitable oxidizing agents include hydrogen peroxide, peracetic acid, perbenzoic acid, alkali metal periodates or mixtures of hydrogen peroxide and an oxidation catalyst, such as tungsten oxide ($WO_3$).

Where the cation M is other than the cation of formula I, the cation can be exchanged to that of formula I by methods known per se. Thus, where $M^+$ is hydrogen, the product can be neutralized with a stoichiometric amount of amine or quaternary ammonium hydroxide, optionally in the presence of an inert diluent, such as water, lower alkanol or mixtures thereof at temperatures between about 0° C. to 100° C. Alternatively, appropriate exchange resins may be used, or the product may be acidified with an inorganic acid to the corresponding free amic acid, separated from the inorganic salt, e.g. where M is an alkali metal, alkaline earth metal or ammonium, and the free amic acid converted to the compound of formula I.

The compounds of formula III are known per se or can easily be perpared by known techniques.

Thus, the compounds of formula III can be prepared by reacting a compound of the formula

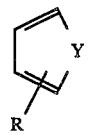
(IV)

wherein Y and R are as defined above, with a compound of the formula

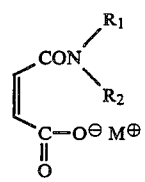
(V)

where $R_1$, $R_2$ and M are as above defined, in the presence of a polar solvent, such as acetone, or an aprotic solvent, such as dimethyl sulfoxide, dimethylsulfone, or dimethylformamide, at a temperature between about 20° and 100° C., to form the corresponding Diels-Alder adduct of formula III. As the artisan can appreciate, by the selection of the appropriate amic acid of formula V, the exo,endo or mixtures of endo and exo,exo, etc. isomers can be obtained.

Alternatively, compounds of formula I can be obtained by reacting a compound of the formula

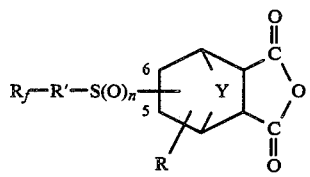
(VI)

where $R_f$, $R_1$, n, R, and Y are as defined above, with an amine of the formula

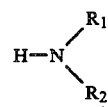
(VII)

where $R_1$ and $R_2$ are as defined above, at a temperature between about 0° C. to about 100° C. in the presence of an inert diluent, such as water or an aqueous/lower alkanol mixture, and optionally converting the amic acid product to the compound of formula I by neutralization, either in situ or as a subsequent step, with an amine, which in the hydroxide form, is represented by the formula

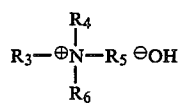
(VIII)

where $R_3$, $R_4$, $R_5$ and $R_6$ are defined above, in an inert diluent, such as water or an aqueous/lower alkanol mixture at a temperature between about 0° C. and about 100° C.

Where $R_1$ and $R_2$ are hydroxyalkyl, it is understood that byproduct esters-amine may form in minor amounts as a by-product.

Where the amido portion of the compound of formula I corresponds to the cationic amine portion of the compound of formula I, the process of the preceding paragraph may be simplified by reacting two moles of the appropriate amine of formula VII per mole of anhydride of formula VI.

In addition, in the reaction of the anhydride of formula VI with the amine of formula VII, it is preferred to add the former to a solution of the latter. This sequence characteristically results in better yields by supression of potentially competing hydrolysis of the anhydride to the acid by insuring an excess of amine during the course of the reaction.

Many of the compounds of formula VI are known, via U.S. Pat. No. 4,082,798, or are easily prepared by techniques known per se.

For example, the anhydrides of formula VI can be prepared by reacting an anhydride of the formula

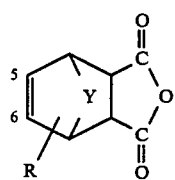

(VIII)

where Y and R are as defined above, with a mercaptan of the formula

$R_f$—R'—S—H     (II)

where $R_f$ and R' are as defined above, in the presence or absence of an inert diluent, such as an aprotic solvent, e.g. dimethylformamide, dimethylsulfoxide, tetrahydrofuran, or an alkanoic acid, such as acetic acid, or a lower alkanol, such as ethanol or alkanol/water mixtures, and a catalytic amount of a free radical initiator, at a temperature between about 0° C. and 100° C. Suitable free radical initiators include those mentioned above in the addition reaction of the mercaptan of formula II with that of formula III.

The resulting compound can be optionally oxidized to form those compounds wherein n is 1 or 2 by the reaction of one or two moles of oxidizing agent per mole of product at a temperature of about 0° C. to about 100° C. in the presence of an inert diluent, such as those mentioned in the preceding paragraph. Again, suitable oxidizing agents include hydrogen peroxide, peracetic acid, perbenzoic acid, alkali metal periodates or mixtures of hydrogen peroxide and an oxidation catalyst, such as tungsten oxide.

In the event hydrolysis occurs, e.g. during the course of the addition reaction between the compounds of formula VIII and II or during optional subsequent oxidation, such that the product of formula VI is converted to the corresponding di-acid, the anhydride can be reformed easily by meeting of the diacid at elevated temperature and/or reduced pressure, e.g. at a temperature of between about 30° C. and 100° C., to remove the water therefrom. Alternatively, the water may be removed by azeotropic distillation e.g. with toluene or benzene, to recover the desired anhydride of formula VI.

The fluoroaliphatic substituted bicycloaliphatic amic acid amine salts may be formulated as aqueous concentrates containing 5% to 60% by weight of the amine salt. Such concentrates are ordinarily clear solutions.

The aqueous concentrate is diluted to an application strength such that the aqueous mixture contains 0.01% to 2% by weight, more preferably between 0.05% and 0.30% by weight of the amine salt, based on the weight of cellulosic or natural or synthetic polyamide substrate.

Suitable cellulosic and natural polyamide substrates for topical application include paper, non-woven fabrics, textiles, paperboard, wood, wood fiber products such as plywood; hair, including wool, hides, leather, and feathers. Synthetic polyamide substrates include nylon fibers and textiles.

For topical application, suitable aqueous mixture contain, advantageously, 0.01% to 5%, preferably 0.02% to 2%, by weight of the amine salts at use dilution based on the weight of aqueous emulsion. Conventional adjuvants such as water repellant assistants, bacteriostats, coloring agents, surface conditioners and the like, may be included, e.g. in an amount of between about 0.01% and 5% by weight in the aqueous mixture. Also, sizing agents, where the mixture is to be used on cellulosic substrates, may be present in amounts of from 0.01% to 10% by weight.

The sizing agent may be a natural sizing agent such as animal glue, asphalt emulsions, wax emulsions, rosins, starches; a semisynthetic sizing agent such as a fatty acid salt or complex, a fortified rosin., e.g., tri sodium maleopimaric acid salt, sodium alginate or sodium carboxymethylcellulose; or a synthetic sizing agent such as an alkylketene dimer, alkylsuccinic anhydrides, polyvinyl alcohol, styrene-maleic anhydride polymers, and the like. Also mixtures thereof may be used.

Asphalt emulsions include those obtained from natural deposits or from the residue of crude petroleum distillation and emulsified in an aqueous solution with an emulsifier such as sodium rosinate or fatty amine. Wax emulsions include those prepared from paraffin waxes, optionally blended with rosin size and emulsified with a suitable emulsifier, such as guar gum, gum arabic, stearic acid salts, lignosulfonate salts, alkylamine salts, and the like. Starches include corn starch, potato starch, wheat starch, ethylated corn starch, cationic corn strch corn starch acetate, and the like. Fatty acid salts and complexes include, for example, stearic acid salts, e.g., of aluminum and zirconium, and the corresponding myristic acid, lauric acid, palmitic acid, margaric acid and behenic acid salts and the corresponding chromium complexes of these acids with chromium salts, including the Werner type complexes of a fatty acid, such as stearic or myristic acid with chromium chloride and isopropanol.

Alkylketene dimers include those wherein the alkyl group is between 6 to 23 carbon atoms such as the palmitic, stearic, oleic and myristic ketene dimers, as well as those where the alkyl group is unsaturated or branched chain, and mixtures thereof.

Alkylsuccinic anhydrides include those where the alkyl group is straight or branched chain and may be saturated or unsaturated having between about 6 to 23 carbon atoms, such as the n-hexadecenylsuccinic anhydride, the dodecylsuccinic anhydride, the dodecenylsuccinic anhydride, the isooctadecenylsuccinic anhydride, and the like.

Also alkylcarbamoyl chlorides, such as ditallowamine carbamoyl chloride; gelatins, cationic aqueous polyurethane emulsions, acrylic resins, stearyl amine surfactants, as known in the art, are suitable sizing agents.

Fillers include materials such as kaolin clay, calcium carbonate, magnesium sulfate, sodium chloride, and the like.

Bacteriostats and fungicides are those commonly used in the paper, leather, fur and textile industries and include halogenated phenols, halogenated carbanilides, o-phenylphenol, salicylic acid anilide, 2,2'-methylene-bis(4-chlorophenol), tetraaliphatic ammonium bromides or chlorides, hydroxyquinoline and the like.

Coloring agents include titanium dioxide, and other conventional inorganic pigments, organic pigments, dyes and optical brighteners.

Surface conditioner adjuvants include paper sizing lubricants, such as a fatty acid/polyethylene glycol stearate mixture; swelling agents, such as an amine oxide swelling agent; extenders, such as urea; filler retention aids, such as colloidal silica and methyl cellulose; and the like.

Also, as discussed below, an emulsifier may also be optionally present in an amount of between about 0.001% to 3% by weight in the composition.

Thus, suitable aqueous compositions for topical application contain
(a) 0.01 to 5% by weight of the amine salt;
(b) 0 to 3% by weight emulsifier;
(c) 0 to 5% water repellant assistant, filler, bacteriostat, coloring agent or surface conditioner adjuvant;
(d) 0 to 10% sizing agent, and
(e) the remainder water.

These aqueous compositions are applied to the surface of the cellulosic or natural or synthetic polyamide material by conventional techniques, including padding, spraying, coating, washing, and brushing. After application, the treated surface is dried, with or without an intermediate washing stage. The resulting surface is thus rendered water and oil resistant.

For use as an internal sizing agent to obtain oil and water repellency, the dilution of the instant aqueous compositions advantageously contain from about 0.0005 to 0.2% by weight of the instant amine salts of formula I. The concentrates for dilution may be prepared as a concentrate containing between 5% and 60% by weight preferably 15 to 45% by weight, of the amine salt of formula I, based on the amount of water.

In order to insure stability of the amine salt in the aqueous medium, the internal sizing compositions are optionally prepared in the presence of a conventional emulsifier. Suitable emulsifiers include anionic, amphoteric and non-ionic emulsifiers. It is preferred to use non-ionic emulsifiers, such as block copolymers or ethylene oxide and propylene oxide.

The amount of emulsifier used, will, of course depend upon the emulsification characterisitcs of the amine salt chosen, as well as the desired concentration of the amine salt in the aqueous medium. Where concentrated emulsions are desired, having between 10 and 40% by weight of the amine salt, it is convenient to use up to 5% of emulsifier. In many cases, little or no emulsifier need be added to obtain a clear stable, aqueous compositions.

Preferably, when present, the emulsifier is present in the emulsion concentrate in an amount between 0.01 and about 3% by weight.

Suitable emulsifiers for use in the present invention include conventional emulsifiers which are compatible with the active amic acid amine salts of formula I.

Preferred emulsifiers are non-ionic emulsifiers including ethoxylated long chain aliphatic amines, ethoxylated long chain aliphatic esters, ethers and thioethers, ethoxylated alkylphenols, block copolymers of ethylene oxide and propylene oxide, and block copolymers of ethylene oxide and propylene oxide on an alkylene polyamine.

Most preferred nonionic emulisifiers are ethylene oxide/propylene oxide block copolymers, polyethoxylated octyl and nonyl phenols, and block copolymers of ethylene oxide and propylene oxide on ethylene diamine. Suitable nonionic emulsifers are widely commercially available, such as Pluronics, including Pluronic F-68, F-87 and F-98 from BASF Wyandotte Corp., Tritons, including Triton X-35 and X-114 from Rohm and Haas Corp.; Igepals; including Igepal CO-710 and CO-730 from GAF Corp.; and Tetronics, such as Tetronic 904, from BASF Wyandotte Corp.

Pluronics are prepared by condensing ethylene oxide with a hydrophobic base formed by the condensation of propylene oxide with propylene glycol and may be represented empirically by the formula:

$$HO-(C_2H_4O)_a(C_3H_6O)_b(C_2H_4O)_cH.$$

Pluronic F-68 contains about 80% ethylene oxide units ($C_2H_4O$) and the molecular weight of the polypropylene oxide block ($C_3H_6O)_b$ is about 1,750. Pluronic F-87 contains about 70% ethylene oxide units ($C_2H_4O$) and the molecular weight of the polypropylene oxide block ($C_3H_6O)_b$ is about 2,250. Pluronic F-98 contains about 80% ethylene oxide units ($C_2H_4O$) and the molecular weight of the polypropylene oxide block ($C_3H_6O)_b$ is about 2,750.

Triton nonionic alkylphenol surfactants are ethoxylated t-octylphenols or ethoxylated nonylphenols. Triton X-35 is an ethoxylated octylphenol having 3 ethylene oxide units and Triton X-114 is likewise an ethoxylated octylphenol having 7 to 8 ethylene oxide units, Igepal CO-710 is an ethoxylated nonylphenol having 71% combined ethylene oxide units by weight of nonylphenol and Igepal CO-730 is an ethoxylated nonylphenol having 73% combined ethylene oxide units by weight of nonylphenol.

Tetronic 904 is an ethylenediamine/propylene oxide ethylene oxide adduct of the approximate formula

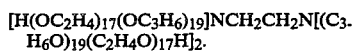

$$[H(OC_2H_4)_{17}(OC_3H_6)_{19}]NCH_2CH_2N[(C_3H_6O)_{19}(C_2H_4O)_{17}H]_2.$$

While the instant aqueous emulsions are suitable for rendering a variety of cellulosic and natural and synthetic polyamide materials oil and water repellant, the instant emulsions are particularly advantageous in rendering articles made from paper pulp, such as paper trays, paper plates and analogous paper articles, both oleophobic and hydrophobic.

In order to further increase the efficiency of application of the aqueous sizing compositions to the paper pulp, it is desirable to pre-treat the paper pulp with a cationic agent, such as cationically modified starch, which is adsorbed by the paper pulp and, consequently, tends to increase the amount of fluorochemical transferred from the aqueous emulsion to the cellulose substrate.

Suitable cationic agents, conventionally used to pretreat cellulose materials such as paper pulp, include conventional cationic modified starches, such as Interbond C, Lok-Size 30, Cato 2, Cato 15 and Cato 17; cationic modified aminoplast resins such as Kymene 557 from Hercules Inc.; cationic polymers such as Santo- Res 21 from Monsanto or Reten-210 from Hercules Inc.; and cationic blocked polyurethanes such as Hypol WB-4000 from W.R. Grace Inc.

Cationic starches are prepared by reacting the starch with amines or quaternary ammonium compounds. Thus, amino ethers of starch are produced by reacting starch with a dialkylaminoalkyl halide which has the amino group in the beta-position, as disclosed, for example, in U.S. Pat. No. 2,970,140 and Canadian Pat. No. 699,812, both of which describe useful cationic starches. Further useful cationic starches are described in U.S. Pat. Nos. 2,876,217 and 3,346,563.

Jointly with the fluoroaliphatic substituted bicycloaliphatic amic amine salts of the invention, can be added one or more of wide choice of water proofing sizing agents selected from classes such as alkyl anhydrides, e.g. Fibron 68; alkyl ketene dimers e.g. Aquapel 360 XC or Hercon 40: polyurethane emulsions, e.g. Graphsize C; acrylic resins, e.g. Carboset; stearyl amine surfactants, e.g., Ethomeen 18/25 complexed with a fatty acid, e.g. stearic acid; Neofat 14, Neofat 47b or Hystrene 9718.

The amount of adjuvant and sizing agent used for treating paper pulp is of the range specified for topical application, supra.

Thus, for internal sizing of paper pulp suitable aqueous compositions contain (a) 0.005 to 0.1% by weight of the instant amine salts;
(b) 0 to 0.05% by weight emulsifier;
(c) 0 to 5% by weight filler, bacteriostat, fungicide, coloring agent or surface conditioner adjuvant;
(d) 0 to 10% sizing agent; and
(e) the remainder water.

The following examples are intended for illustrative purposes only, and are not intended to restrict the scope of the invention in any way. All parts are by weight unless otherwise specified.

EXAMPLE 1 exo-5-(1,1,2,2-tetrahydroperfluorodecylthio)-bicyclo(2,2,2)octane-endo, endo-2,3-dicarboxylic acid anhydride (Table I, F)

In a 100 ml round bottom flask fitted with a nitrogen inlet tube, a reflux condenser, a dropping funnel, and stirred by magnet bar was placed endo-bicyclo(2,2,2)octene-2,3-dicarboxylic acid anhydride (4.0 g, 0.0224 mole), 1,1,2,2-tetrahydroperfluorodecanethiol (10.8 g, 0.0224 mole) and methyl cellosolve acetate (20 g). The solution was heated under a nitrogen atmosphere to 80° C. And 2-tert-butylazo-2-cyanopropane (0.2 g) was dissolved in methyl cellosolve acetate (10.0 g) and the solution was added slowly. This catalyst charge was repeated six times over a three day period. The reaction was terminated at 37% completion (by G.C.) and the mixture was subjected to steam distillation for 3 hours. A crystal slurry in water was formed. The solid material was collected on a Buchner funnel, dried, and subjected to sublimation (90°–100° C., 0.4 torr, 24 hours). The residue was pure product (4.5 g) m.p. 124°–126° C.

Analysis calc. for $C_{10}H_{15}F_{17}SO_3$: 36.3%C, 2.3%H, 48.8%F, 5.4%S. Found: 36.6%C, 2.15%H, 48.4%F, 5.4%S.

EXAMPLE 2 exo-5-(1,1,2,2-Tetrahydroperfluorodecylsulfonyl)-2,3-methylnorbornane dicarboxylic acid anhydride [endo,endo/exo,exo isomer mixture (approx. 1:1)] (Table I, G)

Exo-5-(1,1,2,2-tetrahydroperfluorodecylsulfonyl)-2,3-methylnorbornane dicarboxylic acid (isomer mixture) (20.0 g, 0.0282 mole) was heated in a draft oven (150° C., 15 hours). The product was dissolved in hot toluene and treated with activated carbon. After filtration most of the solvent was stripped off. The residue was cooled and the crystalline product collected (17.0 g, 85% yield).

Anal. Calcd. for $C_{20}H_{15}F_{17}O_5S$: 46.78%F. Found: 46.5% F IR(perchloroethylene): 1855 (strong) and 1773 cm$^{-1}$. (very strong) (>C=o. anhydride).

TABLE I

Perfluoroalkylthio Group Containing Dicarboxylic Acid Anhydrides

| Designation for subsequent examples | Structure | Configuration of anhydride function | $R_f$-distribution (%) | | | | | | |
|---|---|---|---|---|---|---|---|---|---|
| | | | $C_4F_9-$ | $C_6F_{13}-$ | $C_8F_{17}-$ | $C_{10}F_{21}-$ | $C_{12}F_{25}-$ | $C_{14}F_{29}-$ | $>C_{16}F_{33}$ |
| A$_1$ | $R_fCH_2CH_2S$ (bicyclic anhydride structure) | endo | 4 | 95 | 1 | — | — | — | — |
| A$_2$ | " | " | 3 | 31 | 65 | 1 | — | — | — |
| A$_3$ | " | " | — | 4 | 93 | 3 | — | — | — |
| A$_4$ | " | " | — | 4 | 96 | — | — | — | — |
| A$_5$ | " | " | — | — | 100 | — | — | — | — |
| A$_6$ | " | " | 2 | 39 | 34 | 14 | 8 | 3 | — |
| A$_7$ | " | " | 1 | 2 | 16 | 57 | 1 g | 4 | 1 |
| A$_8$ | " | " | — | 3 | 10 | 25 | 35 | 18 | 9 |
| B$_1$ | " | blend of endo and exo prod. (approx. 1:1) | 4 | 95 | 1 | — | — | — | — |
| B$_2$ | " | blend of endo and exo prod. (approx. 1:1) | 3 | 31 | 65 | 1 | — | — | — |

TABLE I-continued
Perfluoroalkylthio Group Containing Dicarboxylic Acid Anhydrides

| Designation for subsequent examples | Structure | Configuration of anhydride function | $R_f$-distribution (%) | | | | | | |
|---|---|---|---|---|---|---|---|---|---|
| | | | $C_4F_9-$ | $C_6F_{13}-$ | $C_8F_{17}-$ | $C_{10}F_{21}-$ | $C_{12}F_{25}-$ | $C_{14}F_{29}-$ | $>C_{16}F_{33}$ |
| $B_3$ | " | blend of endo and exo prod. (approx. 1:1) | — | 4 | 93 | 3 | — | — | — |
| $B_4$ | " | blend of endo and exo prod. (approx. 1:1) | — | 4 | 96 | — | — | — | — |
| $B_5$ | " | blend of endo and exo prod. (approx. 1:1) | — | — | 100 | — | — | — | — |
| $B_6$ | " | blend of endo and exo prod. (approx. 1:1) | 2 | 39 | 34 | 14 | 8 | 3 | — |
| $B_7$ | " | blend of endo and exo prod. (approx. 1:1) | 1 | 2 | 16 | 57 | 19 | 4 | 1 |
| $B_8$ | " | blend of endo and exo prod. (approx. 1:1) | 1 | 40 | 32 | 17 | 7 | 2 | 1 |
| $B_9$ | " | blend of endo and exo prod. (approx. 1:1) | — | 3 | 10 | 25 | 35 | 18 | 9 |
| C | $C_8F_{17}CH_2CH_2S$-(norbornane dicarboxylic anhydride) | exo | | | | | | | |
| D* | $(CF_3)_2CFO(CF_2)_nCH_2CH_2S$-(norbornane dicarboxylic anhydride) | endo | | | | | | | |
| E | $C_8F_{17}CH_2CH_2S$-(methyl norbornane dicarboxylic anhydride), $CH_3$ | blend of endo and exo prod. (approx. 1:1) | | | | | | | |
| F | $C_8F_{17}CH_2CH_2S$-(norbornane dicarboxylic anhydride) | endo | | | | | | | |
| G | $C_8F_{17}CH_2CH_2SO_2$-(methyl norbornane dicarboxylic anhydride), $CH_3$ | blend of endo and exo prod. (approx. 1:1) | | | | | | | |

*n = 6 (70%), n = 8 (30%)

EXAMPLES 3-11

This group of examples illustrates a number of the amines which are useful for the preparation of mono amide mono salts of this invention.

Five gram portions of the fluoro chemical diacid anhydride $A_4$ in Table I were added to a solution of the amines (listed in Table II) in 25 ml of water. The mixture was stirred vigorously and heated to 80° C. (15 min.). After cooling samples were taken and characterized by IR spectroscopy after evaporating of most of the water.

The product in example 5 was isolated by evaporating the water in a draft oven and then under vacuum (0.1 torr) over phosphoric pentoxide. In almost quantitative yield a glassy product was obtained.

Analysis Calcd. for $C_{27}H_{35}F_{17}N_2O_7S$: 37.95%C, 4.13%H, 3.28%N, 37.79%F, 3.75%S. Found: 37.9%C, 4.1%H, 3.5%N, 37.7%F, 4.0%S.

TABLE II

| Example | Amine | grams of amine used | mole ratio R$_f$-anhydride amine | IR-analysis |
|---|---|---|---|---|
| Examples 3-13 | | | | |
| 3 | Monoethanolamine H$_2$NCH$_2$CH$_2$OH | 0.97 | 1:2.05 | amide I (1680 cm$^{-1}$, very strong) amide II, salt (1570 cm$^{-1}$, strong) ester (1760 cm$^{-1}$, very weak) |
| 4 | Diethanolamine HN(CH$_2$CH$_2$OH)$_2$ | 1.67 | 1:2.0 | amide I (1620 cm$^{-1}$, strong) salt (1565 cm$^{-1}$, strong) |
| Examples 1-11 | | | | |
| 5 | AMP (IMC) (CH$_3$)$_2$C—CH$_2$OH NH$_2$ | 1.42 | 1:2.05 | amide I (1620 cm$^{-1}$, weak) amide II, salt (1540 cm$^{-1}$, strong) ester (1740 cm$^{-1}$, weak) |
| 6 | Tris (HOCH$_2$)$_3$—CNH$_2$ | 1.92 | 1:2.05 | amide I (1630 cm$^{-1}$, shoulder) amide II, salt (1520, 1550 cm$^{-1}$, strong) ester (1740 cm$^{-1}$, strong) |
| 7 | Diisopropylamine HN[CH(CH$_3$)$_2$]$_2$ | 1.62 | 1:2.05 | amide I (1625 cm$^{-1}$, weak) salt (1580 cm$^{-1}$, strong) |
| 8 | Morpholine HN(—CH$_2$CH$_2$—)$_2$O | 1.38 | 1:2.05 | amide I (1635 cm$^{-1}$, very strong) salt (1570 cm$^{-1}$, strong) |
| 9 | N—Methyl taurine sodium salt HN(CH$_3$)CH$_2$CH$_2$SO$_3$Na | 2.56 | 1:2.05 | amide (1620 cm$^{-1}$, strong) salt (1565 cm$^{-1}$, strong) |
| 10 | Diisopropanolamine HN[CH$_2$CH(OH)CH$_3$]$_2$ | 1.86 | 1:2.05 | amide (1620 cm$^{-1}$, strong) salt (1565 cm$^{-1}$, very strong) salt (1720 cm$^{-1}$, weak) |
| 11 | N—Methyl glucamine HN(CH$_3$)C$_6$H$_{13}$O$_5$ | 3.10 | 1:2.05 | amide (1610 cm$^{-1}$, strong) salt (1560 cm$^{-1}$, strong) |

EXAMPLE 12

The mono diethanolamide mono diethanolamine salt of exo-5-(1,1,2,2-tetrahydroperfluorodecylthio)-endo, endo-2,3-norbornane dicarboxylic acid by aminolysis of the fluorinated norbornane dicarboxylic acid mono methylester was prepared as follows:

Exo-5-(1,1,2,2-Tetrahydroperfluorodecylthio)-endo,endo-2,3-norbornane dicarboxylic acid mono methylester (U.S. Pat. No. 4,082,798) (8.0 g, 0.0118 mole) and diethanol amine (16.0 g, 0.152 mol) were combined and heated 90° C. under vacuum for 3 hours. IR shows reaction to be mostly complete. IR (film on NaCl): amide I (1620 cm$^{-1}$, strong), salt (1565 cm$^{-1}$, strong).

EXAMPLE 13

The mono diethanolamide mono diethanolamine salt of exo-5-(1,1,2,2tetrahydroperfluorodecylthio)-endo,endo-2,3-norbornane dicarboxylic acid by reaction of the nonfluorinated norbornane dicarboxylic acid mono amide mono acid was prepared as follows:

(a) Monomethyl 5-norbornene-endo,endo-2,3-dicarboxylate (50.0 g, 0.25 mole) was combined with diethanolamine (60.0 g, 0.55 mole) and heated to 140°-145° C. till methanol evolution ceased. Most of the theoretical yield for methanol was obtained (9.0 ml). The product, a clear amber glass was characterized by IR and used without further purification.

(b) The product obtained in example 13a (50.0 g, 0.124 mole) was dissolved in water (50 ml). The solution was placed in a 500 ml flask fitted with stirrer, nitrogen inlet, dropping funnel, and reflux condenser. Isopropanol (200 ml) and 1,1,2,2-tetrahydroperfluorodecanethiol (54.3 g, 0.113 mol) were charged. The mixture was brought to reflux under nitrogen atmosphere and a solution of 2,2'-azobis(2,4-dimethylvaleronitrile in isopropanol (1%, 20 g) was added dropwise. After 1 hour all mercaptan was consumed. Excess mercaptan (10 g) was added and the reaction held at reflux for another 2 hours. The solvent was evaporated under vacuum and the residue was washed with methyl ethyl ketone. A gummy solid was obtained and the structure was confirmed by IR.

EXAMPLES 14-19

These examples demonstrate how the R$_f$-diacid anhydrides can be converted in mono amid mono carboxylic acid salts and useful emulsions or solutions simultaneously, in one operation, by weighing amine Pluronic F-68 (wetting aid, from BASF Wyandotte), anhydride A$_4$ (Table I) and water into a 2 ounce jar. The contents were stirred at 70°-80° C. for 10 minutes. Amounts see Table III.

TABLE III

Examples 14-19

Aqueous Formulations of

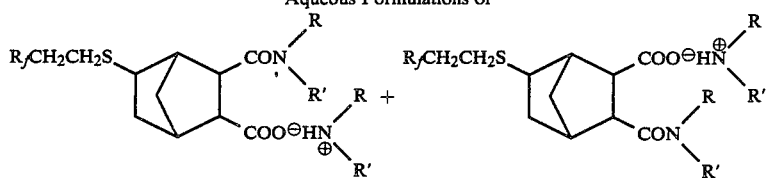

| Example | made from 4 g A₄ (Table I) and the following amine | weight of dist. water | weight of 10%, solution of Pluronic F-68 | calculated solids content | Appearance | pH of a 1% dilution (w/v) in water |
|---|---|---|---|---|---|---|
| 14 | 1.31 g diethanol amine (example 5) | 16.4 g | 4.40 g | 22.0% | nearly clear, low viscous liquid | 9.15 |
| 15 | 1.92 g AMP example (5) | 15.70 g | 4.40 g | 22.0% | milky white, free flowing liquid | 8.7 |
| 16 | 1.08 g Morpholine (example 8) | 15.61 g | 4.40 g | 22.0% | clear, low viscous liquid | 8.7 |
| 17 | 1.60 g Diisopropanolamine (example 10) | 17.46 g | 4.40 g | 22.0% | light hazy, viscous liquid | 8.7 |
| 18 | 3.36 g N—Methyltaurine sodium salt (example 9) | 18.42 g | 4.40 g | 22.0% | clear, low viscous liquid | 8.85 |
| 19 | 2.67 N—Methylglucamine (example 11) | 21.33 g | 4.40 g | 22.0% | hazy, low viscous liquid | 9.1 |

EXAMPLES 20-41

The use of a number of other fluorinated anhydrides is described in this group of examples.

Using the methods and techniques described in examples 14-19, the examples listed in Table IV are prepared.

used to impart oil and water repellent properties to a variety of substrates.

TABLE IV

Examples 20-41

| Example | Wgt. of $R_f$ Anhydride, Typ (Table I) | Wgt. of water | Wgt. of pluronic F-68* | Wgt. of Diethanol amine | Calc. % solids | Appearance | pH of a 1% dilution on water |
|---|---|---|---|---|---|---|---|
| 20 | 4.00 g A₇ | 12.38 g | 4.40 g | 1.69 g | 22.0 | cloudy, low viscous liquid | 9.07 |
| 21 | 4.00 g A₂ | 16.786 | 4.41 g | 1.56 g | 22.0 | milky white, low viscous liquid | 9.00 |
| 22 | 4.00 g A₃ | 16.81 g | 4.40 g | 1.42 g | 22.0 | clear, low viscous liquid | 9.10 |
| 23 | 4.00 g A₄ | 16.4 g | 4.40 g | 1.31 g | 22.0 | milky white, low viscous liquid | 9.15 |
| 24 | 4.00 g A₅ | 16.4 g | 4.40 g | 1.31 g | 22.0 | clear, slightly viscous liquid | 9.06 |
| 25 | 4.00 g A₆ | 16.99 g | 4.40 g | 1.47 g | 22.0 | opaque, low viscous liquid | 9.24 |
| 26 | 4.00 g A₇ | 15.22 g | 4.40 g | 1.11 g | 22.0 | opaque, low viscous liquid | 9.24 |
| 27 | 4.00 g A₉ | 15.99 g | 4.40 g | 1.17 g | 22.0 | opaque, straw colored | 9.0 |
| 28 | 4.00 g B₁ | 18.69 g | 4.40 g | 1.95 g | 22.0 | cloudy, sl. yellow, low viscous liquid | 8.7 |
| 29 | 4.00 g B₂ | 18.10 g | 4.40 g | 1.80 g | 22.0 | clear, yellowish low viscous liquid | 9.05 |
| 30 | 4.00 g B₃ | 16.45 g | 4.40 g | 1.32 g | 22.0 | clear, low viscous liquid | 8.89 |
| 31 | 4.00 g B₄ | 16.39 g | 4.40 g | 1.30 g | 22.0 | hazy, low viscous liquid | 8.93 |
| 32 | 4.00 g B₅ | 18.87 g | 4.40 g | 2.00 g | 22.0 | clear, low viscous liquid | 8.74 |
| 33 | 4.00 g B₆ | 16.53 g | 4.40 g | 1.61 g | 22.8 | clear, low viscous liquid | 8.98 |
| 34 | 4.00 g B₇ | 15.72 g | 4.40 g | 1.22 g | 22.3 | cloudy, low viscous liquid | 9.01 |
| 35 | 4.00 g B₈ | 16.97 g | 4.40 g | 2.05 g | 23.7 | cloudy, light amber, low viscous liquid | 8.9 |
| 36 | 4.00 g B₉ | 15.99 g | 4.40 g | 1.17 g | 21.9 | opaque, straw colored | 8.9 |
| 37 | 4.00 g C | 17.38 g | 4.40 g | 1.58 g | 22.0 | clear, low viscous liquid | 9.1 |
| 38 | 4.00 g D | 16.21 g | 4.40 g | 1.25 g | 22.0 | clear, straw colored | 8.9 |
| 39 | 4.00 g E | 16.31 g | 4.40 g | 1.28 g | 22.0 | clear, low viscous liquid | 8.75 |
| 40 | 2.00 g F | 8.38 g | 2.20 g | 0.70 g | 22.0 | low viscous liquid with precipitation | 8.56 |
| 41 | 4.00 g G | 17.13 g | 4.40 g | 1.34 g | 22.0 | clear, amber, low viscous liquid | 8.94 |

*As 10% (w/v) solution in water

The following examples illustrate how the compounds and dispersions of the previous examples can be

Application Examples

EXAMPLE 42

OIL KIT for Surface Oil Resistance Tests (TAPPI method UM-557)

An easily made kit of twelve solutions of varying proportions of Castor Oil, Toluene, and Heptane is useful in comparing surface oil resistance.

| Kit No. | Volume Castor Oil | Volume Toluene | Volume Heptane |
|---|---|---|---|
| 1 | 200 | 0 | 0 |
| 2 | 180 | 10 | 10 |
| 3 | 160 | 20 | 20 |
| 4 | 140 | 30 | 30 |
| 5 | 120 | 40 | 40 |
| 6 | 100 | 50 | 50 |
| 7 | 80 | 60 | 60 |
| 8 | 60 | 70 | 70 |
| 9 | 40 | 80 | 80 |
| 10 | 20 | 90 | 90 |
| 11 | 0 | 100 | 100 |
| 12 | 0 | 90 | 110 |

The "kit value" is defined as the highest number solution that will stand on the surface of the plate for 15 seconds in the form of drops without failing. Failure is detected by pronounced darkening caused by penetration. The darkening of even a small fraction of the area under the drop is considered failure.

This example demonstrates the utility of these dispersions as internal sizes.

Six grams of dry bleached Kraft pulp were diluted in 289 ml distilled water and thoroughly dispersed in a blender. To this pulp slurry was added 4.7 ml of a 1% dilution (as is) of the dispersion from example 24 in distilled water. This was mixed in for 5 minutes, then 6 ml of a 1% aqueous solution of cooked cationic starch was added. This was mixed together for an additional 5 minutes. To this, 1.2 ml of a 1.5% (on solids) dilution of an alkyl ketene dimer emulsion was added as a water repellent adjuvant. This was mixed in for another 10 minutes. The resulting slurry was diluted with an additional 500 ml of dist. water and mixed again. This mixture was then poured over a 100 mesh wire screen, with a vacuum applied from below which pulled the water from the pulp mixture to form a sheet on the screen. The wet sheet was removed from the screen and dried between another screen and hard surface at a pressure of approximately 0.4 lbs/in.$^2$ at 110° C. for 1½ hours.

The paper formed in this manner, showed a TAPPI method UM-557 oil kit number of 4.

One ml of hot (110° C.) corn oil placed on the paper remained on the surface and did not penetrate for 20 minutes. Similarly, 1 ml of hot (80° C.) water containing 0.5% of Triton X-165 wetting agent (from Rohm & Haas) placed on the paper did not penetrate for 20 minutes. Whereas, paper made in the same manner, including the cationic starch and water repellant adjuvant but without the fluorochemical dispersion; demonstrated an oil kit number of <1, and held the hot corn oil and hot water/Triton X-165 solution for less than one minute (began to penetrate as soon as applied).

EXAMPLES 43–46

In these examples the utility of various other mono amid mono carboxylic acid amine salts prepared from different fluorinated anhydrides prepared by the method described in examples 14–19 is demonstrated. The fluorochemical dispersions were evaluated by the method of example 42. They show the performance as listed in Table V.

TABLE V

| | | Examples 43-46 | | | | | |
|---|---|---|---|---|---|---|---|
| Example | Fluorochemical | Fluorine on wgt. of paper | Cationic starch on paper | Alkyl ketene dimer adjuvant in paper | Oil test number | Hot, 110° C. corn oil | Hot, 80° C. water + 0.5% Triton X-165 |
| 43 | aqueous formulation prepared as in example 15 | 0.05 / 0.06 | 1.0% / 1.0% | 0.3% / 0.3% | 3 / 4 | 10 min. / >20 min. | >20 min. / >20 min. |
| 44 | aqueous formulation prepared as in example 17 | 0.05 / 0.06 | 1.0% / 1.0% | 0.3% / 0.3% | 3 / 3-4 | 2 min. / >20 min. | >20 min. / >20 min. |
| 45 | aqueous formulation prepared as in example 39 | 0.05 / 0.06 | 1.0% / 1.0% | 0.3% / 0.3% | 4 / 4 | >20 min. / >20 min. | >20 min. / >20 min. |
| 46 | aqueous formulation prepared as in example 41 | 0.05 / 0.06 | 1.0% / 1.0% | 0.3% / 0.3% | 3 / 5 | 2 min. / >20 min. | >20 min. / >20 min. |

We claim:

1. A process for rendering a cellulosic or natural or synthetic polyamide substrate oil and water repellant comprising
    (A) contacting said substrate with an oil and water repellant imparting effective amount of an aqueous emulsion comprising
    (a) 0.01% to 5% by weight of a fluoroaliphatic substituted bicycloaliphatic amic acid amine salt of the formula

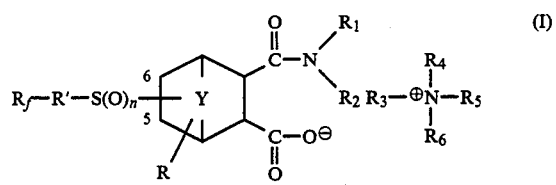

wherein $R_f$ is straight or branched chain perfluoroalkyl of 4 to 18 carbon atoms or perfluoroalkoxy-perfluoroalkyl of 4 to 18 carbon atoms;

R' is straight or branched chain alkylene of 1 to 12 carbon atoms, alkylenethioalkylene of 2 to 12 carbon atoms, alkyleneoxyalkylene of 2 to 12 carbon atoms, or alkyleneiminoalkylene of 2 to 12 carbon atoms where the imino nitrogen atom contains as a third substituent, hydrogen or alkyl of 1 to 6 carbon atoms;

n is 0, 1 or 2;

Y is lower alkylene or —O—;

$R_1$ and $R_2$ are independently hydrogen, lower alkyl, hydroxy-lower alkyl, or together with the nitrogen to which they are attached, represent morpholino;

$R_3$, $R_4$ and $R_5$ independently represent hydrogen, lower alkyl, or hydroxy-lower alkyl, $R_6$ is lower alkyl, benzyl, lower alkyl substituted by hydroxy, carboxy or sulfo, or together with $R_5$ and the nitrogen to which they are attached represent morpholino;

R is hydrogen or methyl; and wherein the $R_f$—R'—S(O)$_n$— group is in the 5- or 6-position (b) 0%–3% by weight emulsifier;

(c) 0%–5% by weight filler, water repellant assistant, coloring agent, or surface conditioner adjuvant;

(d) 0%–10% by weight sizing agent; and (e) the remainder water; and (B) drying the treated substrate.

2. A process for the internal sizing of paper pulp and rendering said pulp oil and water repellant comprising (A) contacting said paper pulp with an internal sizing and oil and water repellant imparting effective amount of an aqueous emulsion comprising (a) 0.0005–0.1% by weight of an amine salt of the formula $$R_f\text{—}R'\text{—}S(O)_n\underset{5}{\overset{6}{\underset{R}{\bigcirc}}}Y\underset{\underset{O}{\overset{\|}{C}}\text{—}O^\ominus}{\overset{\overset{O}{\overset{\|}{C}}\text{—}N\overset{R_1}{\underset{R_2}{}}}{}}\quad R_3\text{—}\overset{R_4}{\underset{R_6}{\overset{\oplus}{N}}}\text{—}R_5 \quad (I)$$

wherein $R_f$ is straight or branched chain perfluoroalkyl of 4 to 18 carbon atoms or perfluoroalkoxy-perfluoroalkyl of 4 to 18 carbon atoms;

R' is straight or branched chain alkylene of 1 to 12 carbon atoms, alkylenethioalkylene of 2 to 12 carbon atoms, alkyleneoxyalkylene of 2 to 12 carbon atoms, or alkyleneiminoalkylene of 2 to 12 carbon atoms where the imino nitrogen atom contains as a third substituent, hydrogen or alkyl of 1 to 6 carbon atoms;

n is 0, 1 or 2;

Y is lower alkylene or —O—;

$R_1$ and $R_2$ are independently hydrogen, lower alkyl, hydroxy-lower alkyl, or together with the nitrogen to which they are attached, represent morpholino;

$R_3$, $R_4$ and $R_5$ independently represent hydrogen, lower alkyl, or hydroxy-lower alkyl, $R_6$ is lower alkyl, benzyl, lower alkyl substituted by hydroxy, carboxy or sulfo, or together with $R_5$ and the nitrogen to which they are attached represent morpholino;

R is hydrogen or methyl; and wherein the $R_f$—R'—S(O)$_n$— group is in the 5- or 6-position (b) 0.00001 to 0.05% by weight emulsifier (c) 0 to 5% by weight filler, bacteriostal, fungicide, coloring agent or surface conditioner adjuvant;

(d) 0 to 10% sizing agent; and (e) the remainder water; to render said pulp oil and water repellant, and (B) subsequently drying said contacted pulp.

3. A process according to claim 2, wherein said paper pulp is pretreated with a cationic agent.

4. A process according to claim 2, wherein the cationic agent is a cationically modified starch, a cationic modified aminoplast resin, a cationic polymer or a cationic blocked polyurethane.

5. A process according to claim 3, wherein the cationic agent is a cationically modified starch.

6. A water and oil repellant cellulosic, or natural o r synthetic polyamide, substrate produced according to the process of claim 1.

7. An oil and water repellant paper pulp article produced according to the process of claim 2.

8. An oil and water repellant paper pulp article produced according to the process of claim 4.

* * * * *